(12) United States Patent
Casey et al.

(10) Patent No.: US 8,372,644 B2
(45) Date of Patent: Feb. 12, 2013

(54) METHOD FOR GROWING ADULT CELLS

(75) Inventors: Patrick J. Casey, Kumeu (NZ); Richard Fry, Kumeu (NZ); Kerri Fry, Kumeu (NZ)

(73) Assignee: Transplantation Limited, Kumeu (NZ)

( * ) Notice: Subject to any disclaimer, the term of this patent is extended or adjusted under 35 U.S.C. 154(b) by 1274 days.

(21) Appl. No.: 11/702,895

(22) Filed: Feb. 6, 2007

(65) Prior Publication Data

US 2008/0009059 A1      Jan. 10, 2008

Related U.S. Application Data

(60) Provisional application No. 60/765,668, filed on Feb. 6, 2006.

(51) Int. Cl.
*C12N 5/00*      (2006.01)

(52) U.S. Cl. ......... 435/379; 435/380; 435/381; 435/395

(58) Field of Classification Search ........................ None
See application file for complete search history.

(56) References Cited

U.S. PATENT DOCUMENTS 7,022,518 B1 *   4/2006  Feye .......................... 435/297.1

FOREIGN PATENT DOCUMENTS

WO       WO 0146401  A1 *  6/2001

* cited by examiner

*Primary Examiner* — Jim Ketter
(74) *Attorney, Agent, or Firm* — Preti Flaherty Beliveau & Pachios LLP

(57) ABSTRACT

A method for growing adult cells includes harvesting a tissue sample from a subject and breaking the tissue sample into fragments. The fragments are placed into a culture vessel, and at least some of the fragments are induced to adhere to the culture vessel. The fragments are supplied with nutrients so that adult cells contained therein divide and grow.

10 Claims, No Drawings

METHOD FOR GROWING ADULT CELLS

CROSS REFERENCES TO RELATED APPLICATIONS

This application claims the benefit of U.S. Provisional Application No. 60/765,668, filed Feb. 6, 2006.

BACKGROUND OF THE INVENTION

It is well known that many animal and plant cells may be grown in vitro. However, certain cells, particularly adult or non-embryonic cells, are severely limited in their ability to divide and grow. Cellular growth is not limited by genetic models of memory. Instead, cellular growth is limited by "spatial compaction." For example, organs stop growing due to pressure from the peri or covering material of the organ.

Accordingly, it would be desirable to develop methodologies for processing non-embryonic cells so that the cells grow and divide unimpeded as if they were embryonic cells.

SUMMARY OF THE INVENTION

The above-mentioned need is met by the present invention, one embodiment of which includes a method for growing adult cells that includes harvesting a tissue sample from a subject and breaking the tissue sample into fragments. The fragments are placed into a culture vessel, and at least some of the fragments are induced to adhere to the culture vessel. The fragments are supplied with nutrients so that adult cells contained therein divide and grow.

The present invention and its advantages over the prior art will be more readily understood upon reading the following detailed description.

DETAILED DESCRIPTION OF THE INVENTION

The present invention relates to an in vitro method for growing adult cells from a tissue sample taken from a mammal or other organism. Adult cells grown under specific culture conditions reach confluence and then form structures related to the origin of the cell type. For example, cells originating from an equine nucal ligament can form tendon-like structures in vitro. Other examples include, but are not limited to, porcine pancreatic tissue and articular cartilage. While the present invention is particularly applicable to eutherian and marsupial mammals, it should be noted that the present invention is not limited to mammalian cells. The present invention is also not necessarily limited to structures commonly recognized as organs.

In general, the method comprises harvesting a tissue sample from a patient and breaking the tissue sample down into fragments. The fragments are placed in a culture vessel and induced to attach or adhere to the vessel. Adherence to the vessel will allow the cells to grow and divide. The attached tissue fragments are then supplied with nutrients (for example, but not limited to, immersion in specific cell culture media under predetermined conditions) to induce the proliferation of cells. After a number of cell doublings, the cells can be harvested, packaged and administered back to the patient, thus providing cells of the correct type that avoid rejection.

The tissue sample is typically harvested aseptically and then washed once in PBS (phosphate buffered saline)/PenStrep (penicillin-streptomycin) solution. The tissue sample is then placed in media (e.g., hepes DMEM/F12+10% FCS+PenStrep) at room temperature for transport to the lab. The tissue sample may be processed immediately or kept for a period of time (typically up to 24 hours) at an appropriate temperature, such as 4 degrees Celsius, before processing.

The tissue sample may be fragmented by any suitable technique, including but not limited to dissection, chemical digestion, and physical digestion. Moreover, the tissue fragments may be attached to the vessel using any suitable technique, such as those described below.

When cell growth is about 90% confluent in the culture vessel, cells are removed via Trypsin/EDTA digestion. The cells are counted using a haemocytometer and the suspension then centrifuged. The cells may be frozen or used for therapeutic administration.

For therapeutic samples (e.g., equine tendon), the resulting pellet is re-suspended in about 0.5 ml of PBS and loaded into a 1 ml syringe. The syringe is transported back to patient at room temperature and the suspension administered back to the patient.

EXAMPLES

Dissection

In this example, a tissue sample, such as from equine articular cartilage or porcine pancreatic tissue, is harvested and washed as described above and placed in 2 ml of Media 1 (hepes DMEM/F12+10% FCS+PenStrep) in a glass petri dish. The tissue sample is then dissected into 2×2 mm pieces using sterile scalpel blades. The pieces or fragments are then placed into a 25 ml tissue culture flask with only enough media to keep tissue moist, not suspended. This flask is then flipped over (or partially tipped) and 2 ml of Media 1 is added to the bottom to keep the tissue fragments humidified. With the flask inverted, the fragments are stressed by gravity but tend to remain in contact with the flask surface due to the moisture from the media. The flask is then placed in a 5% $CO_2$/38.5 degree Celsius incubator for 48 hours. During this time, some of the tissue fragments will adhere to the flask surface. After 48 hours, the humidifying media is removed, the flask is flipped upright, and 2 ml of Media 2 (bicarb DMEM/F12+10% FCS) is gently added to bathe and immerse the tissue fragments. Cell growth from the tissue fragments is monitored daily, and media is replaced every 2-3 days. When cell growth is confluent around the tissue fragments, the media is removed and the culture is washed with PBS/PenStrep. The cells are then harvested via Trypsin/EDTA incubation. When most of the cells have detached from the flask surface, the digestion is stopped with the addition of 5-10 mls Media 2. The suspension is then aspirated to break up cell aggregates and then centrifuged. The resulting pellet is re-suspended in Media 2 and the suspension placed in a 75 or 150 ml flask to scale-up cell numbers rapidly.

Chemical Digestion

In this example, a tissue sample, such as from equine articular cartilage or porcine pancreatic tissue, is harvested and washed as described above and placed in 2 ml of Media 1 in a glass petri dish. The tissue sample is then dissected into 2×2 mm pieces using sterile scalpel blades. The pieces or fragments are then incubated with Trypsin/EDTA. The cellular fragments resulting from this incubation are harvested via centrifugation, re-suspended in 2 ml of Media 1, and then placed into a 25 ml tissue culture flask. This flask is then flipped over (or partially tipped), and the 2 ml of Media 1 keep the tissue fragments humidified. With the flask inverted, the fragments are stressed by gravity but tend to remain in contact with the flask surface due to the moisture from the media. The flask is then placed in a 5% $CO_2$/38.5 degree Celsius incubator for 48 hours. During this time, some of the tissue fragments adhere to the flask surface. After 48 hours, the humidifying media is removed, the flask is flipped upright, and 2 ml of Media 2 is gently added to bathe and immerse the tissue fragments. Cell growth from the tissue fragments is monitored daily, and media is replaced every 2-3 days. When cell growth is confluent around the tissue fragments, the media is removed and the culture is washed with PBS/PenStrep. The cells are then harvested via Trypsin/EDTA incubation. When most of the cells have detached from the flask surface, the digestion is stopped with the addition of 5-10 mls Media 2. The suspension is then aspirated to break up cell aggregates and then centrifuged. The resulting pellet is re-suspended in Media 2 and the suspension placed in a 75 or 150 ml flask to scale-up cell numbers rapidly.

Physical Digestion

In this example, a tissue sample, such as from equine articular cartilage or porcine pancreatic tissue, is harvested aseptically. Small pieces of the tissue are forced through a sterile metal sieve. The resulting fragments are washed in a PBS/PenStrep solution and centrifuged three times. The resulting pellet is re-suspended in 2 ml of Media 1 and then placed into a 25 ml tissue culture flask. This flask is then flipped over (or partially tipped), and the 2 ml of Media 1 keep the tissue fragments humidified. With the flask inverted, the fragments are stressed by gravity but tend to remain in contact with the flask surface due to the moisture from the media. The flask is then placed in a 5% $CO_2$/38.5 degree Celsius incubator for 48 hours. During this time, some of the tissue fragments adhere to the flask surface. After 48 hours, the humidifying media is removed, the flask is flipped upright, and 2 ml of Media 2 is gently added to bathe and immerse the tissue fragments. Cell growth from the tissue fragments is monitored daily, and media is replaced every 2-3 days. When cell growth is confluent around the tissue fragments, the media is removed and the culture is washed with PBS/PenStrep. The cells are then harvested via Trypsin/EDTA incubation. When most of the cells have detached from the flask surface, the digestion is stopped with the addition of 5-10 mls Media 2. The suspension is then aspirated to break up cell aggregates and then centrifuged. The resulting pellet is re-suspended in Media 2 and the suspension placed in a 75 or 150 ml flask to scale-up cell numbers rapidly. This methods works well for organs that secrete enzymes and are likely to attract infection when processed via Dissection.

While specific embodiments of the present invention have been described, it should be noted that various modifications thereto can be made without departing from the spirit and scope of the invention as defined in the appended claims.

What is claimed is:

1. A method for growing adult cells comprising:
   harvesting a tissue sample from a subject;
   breaking the tissue sample: into fragments;
   placing the fragments into a culture vessel;
   inducing at least some of the fragments to adhere to the culture vessel by the steps of:
      placing the fragments into the culture vessel;
      adding enough media to keep the fragments moist but not suspended;
      flipping the culture vessel over; and
      incubating the fragments; and
   supplying the fragments with nutrients so that adults cells contained therein divide and grow.

2. The method of claim 1 wherein supplying the fragments with nutrients includes immersing the fragments in a cell culture media.

3. The method of claim 2 wherein said cell culture media is bicarb DMEM/F12+10% FCS.

4. The method of claim 1 wherein incubating the fragments includes placing the culture vessel in a 5% $CO_2$/38.5 degree Celsius incubator.

5. The method of claim 4 wherein the culture vessel is left in the 5% $CO_2$/38.5 degree Celsius incubator for about 48 hours.

6. The method of claim 1 wherein breaking the tissue sample into fragments includes dissection.

7. The method of claim 1 wherein breaking the tissue sample into fragments includes chemical digestion.

8. The method of claim 1 wherein breaking the tissue sample into fragments includes physical digestion.

9. The method of claim 1 further comprising removing cells from the culture vessel after cell growth is about 90% confluent.

10. The method of claim 9 wherein cells are removed via Trypsin/EDTA digestion.

* * * * *